United States Patent [19]

Abel et al.

[11] Patent Number: 5,571,771

[45] Date of Patent: * Nov. 5, 1996

[54] CARRIER CATALYST, PROCESS FOR THE PRODUCTION THEREOF, AND USE THEREOF FOR THE PREPARATION OF VINYL ACETATE

[75] Inventors: Roland Abel, Oberhausen; Karl-Fred Wörner, Hofheim, both of Germany

[73] Assignee: Hoechst Aktiengesellschaft, Germany

[*] Notice: The term of this patent shall not extend beyond the expiration date of Pat. No. 5,559,071.

[21] Appl. No.: 276,438

[22] Filed: Jul. 18, 1994

[30] Foreign Application Priority Data

Jul. 16, 1993 [DE] Germany ............... 43 23 978.1

[51] Int. Cl.$^6$ ............... B01J 23/02; B01J 23/06; B01J 23/40; B01J 23/42
[52] U.S. Cl. ............... 502/330; 502/326; 502/339; 502/340
[58] Field of Search ............... 502/326, 330, 502/339, 340

[56] References Cited

U.S. PATENT DOCUMENTS

| | | |
|---|---|---|
| 3,775,342 | 11/1973 | Kronig et al. . |
| 4,048,096 | 9/1977 | Bissot . |
| 4,305,843 | 12/1981 | Krabetz et al. . |
| 4,370,492 | 1/1983 | Wunder et al. . |
| 4,520,124 | 5/1985 | Abe et al. . |
| 4,902,823 | 2/1990 | Wunder et al. . |
| 5,179,056 | 1/1993 | Bartley . |
| 5,179,057 | 1/1993 | Bartley . |
| 5,185,308 | 2/1993 | Baryley et al. . |
| 5,250,487 | 10/1993 | Wirtz et al. . |
| 5,274,181 | 12/1993 | Bartley . |
| 5,292,931 | 3/1994 | Wirtz et al. . |
| 5,342,987 | 8/1994 | Bartley . |

FOREIGN PATENT DOCUMENTS

| | | |
|---|---|---|
| 0015569 | 9/1980 | European Pat. Off. . |
| 0519436 | 12/1992 | European Pat. Off. . |
| 0519435 | 12/1992 | European Pat. Off. . |
| 0569624 | 11/1993 | European Pat. Off. . |
| 1964085 | 7/1971 | Germany . |
| 3433197 | 3/1985 | Germany . |

Primary Examiner—Anthony Mc Farlane
Assistant Examiner—E. D. Irzinski
Attorney, Agent, or Firm—Connolly & Hutz

[57] ABSTRACT

The invention relates to Pd/K/Au, Pd/K/Ba or Pd/K/Cd supported catalysts built up in the form of an outer layer, the production thereof and the use thereof for preparing vinylacetate from ethylene, acetic acid and oxygen in the gas phase. The specified catalysts are produced by impregnating the support particles with a solution of salts of the corresponding elements and then drying them, with the dynamic viscosity of the solution being at least 0.003 Pa.s and the solution volume in impregnation being more than 80% of the pore volume of the support particles and the duration of the impregnation and also the time until commencement of the drying being selected so as to be sufficiently short for, after completion of the drying, the specified metal salts to be present in an outer layer of from 5% to 80% of the pore volume of the support particles.

12 Claims, No Drawings

CARRIER CATALYST, PROCESS FOR THE PRODUCTION THEREOF, AND USE THEREOF FOR THE PREPARATION OF VINYL ACETATE

BACKGROUND OF THE INVENTION

Description of the Prior Art

It is known that vinyl acetate can be prepared in the gas phase from ethylene, acetic acid and oxygen; the supported catalysts used for this synthesis comprise palladium and an alkali metal element, preferably potassium. Further additives used are cadmium, gold or barium.

In the Pd/K/Au catalysts both noble metals are generally applied in the form of an impregnated layer on the support; they are produced by impregnation and subsequent precipitation of the metal salts by means of alkaline compounds (U.S. Pat. No. 4,048,096, U.S. Pat. No. 3,775,342).

In Pd/K/Ba catalysts the metal salts are applied by impregnation, spraying on, vapor deposition, dipping or precipitation (EP-A-0 519 436). The same methods are known for Pd/K/Cd catalysts (U.S. Pat. No. 4,902,823; U.S. Pat. No. 3,393,199, U.S. Pat. No. 4,668,819). Furthermore, the production of a Pd/K/Au or Pd/K/Cd surface impregnated catalyst is known, with a specific support material being washed with an acid prior to impregnation and being treated with a base after impregnation (EP-A-0 519 435).

The German Patent Application P 42 11 780.1 describes Pd/K/Au, Pd/K/Ba or Pd/K/Cd catalysts built up in the form of an outer layer by atomizing a solution of the corresponding metal salts by means of ultrasound and then, in a limited amount and over a limited time, applying this to the support particles and commencing the drying thereof in such a way that the catalytically active metal salts cannot penetrate into the core of the support particles, but only into an outer part having a greater or lesser thickness, the impregnated layer.

SUMMARY OF THE INVENTION

It has now been found that surface impregnated catalysts containing the specified elements are obtained much more simply by impregnating the support particles with viscous solution of corresponding metal salts, instead of applying a solution after atomization into very fine droplets by means of ultrasound. In this impregnation, the amount of solution has no upper limit, but the impregnation has to be carried out sufficiently quickly and the drying has to be commenced sufficiently quickly, similar to the case of the solution atomized by ultrasound in accordance with P 42 11 780.1.

DESCRIPTION OF THE PREFERRED EMBODIMENTS

The invention provides a process for producing a surface impregnated catalyst comprising palladium, potassium and cadmium on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

The invention also provides a surface impregnated catalyst produced in this manner, and the use thereof for preparing vinyl acetate from ethylene, acetic acid and oxygen in the gas phase.

In this drying, the amount of solution has no upper limit; a higher excess of solution does no harm, but is superfluous.

The invention further provides a process for producing a surface impregnated catalyst comprising palladium, potassium and barium on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

The invention also provides a surface impregnated catalyst produced in this manner, and the use thereof for preparing vinyl acetate from ethylene, acetic acid and oxygen in the gas phase.

Here too, the amount of solution has no upper limit.

The invention further provides a process for producing a surface impregnated catalyst comprising palladium, potassium and gold on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

The invention also provides a surface impregnated catalyst produced in this manner, and the use thereof for preparing vinyl acetate from ethylene, acetic acid and oxygen in the gas phase.

Here too, the amount of solution has no upper limit.

Supports used are inert materials such as silicon dioxide, aluminum oxide or mixtures of these oxides in the form of spheres, pellets, rings, stars or other shaped bodies; the diameter, or the length and thickness, of the support particles is generally from 3 to 9 mm.

The surface area of the supports is, measured by the BET method, generally from 50 to 250 $m^2/g$; the pore volume is generally from 0.4 to 1.2 ml/g.

The metal contents of the finished catalysts are as follows:

The palladium content of the Pd/K/Cd and the Pd/K/Ba catalysts is in general from 0.6 to 3.5% by weight, preferably from 0.8 to 3.0% by weight, in particular from 1.0 to 2.5% by weight. The palladium content of the Pd/K/Au catalysts is in general from 0.5 to 2.0% by weight, preferably from 0.6 to 1.5% by weight.

The potassium content of all three types of catalyst is in general from 0.5 to 4.0% by weight, preferably from 1.5 to 3.0% by weight. The cadmium content of the Pd/K/Cd catalysts is in general from 0.1 to 2.5% by weight, preferably from 0.4 to 2.0% by weight. The barium content of the Pd/K/Ba catalysts is in general from 0.1 to 2.0% by weight, preferably from 0.2 to 1.0 % by weight. The gold content of the Pd/K/Au catalysts is in general from 0.2 to 1.0% by weight, preferably from 0.3 to 0.8 % by weight.

Suitable salts are all salts of palladium, cadmium, barium, gold and potassium which are soluble and contain no constituents, e.g. sulfur, which poison the catalyst; preference is given to the acetates and the chlorides. However, in the case of the chlorides, it must be ensured that the chloride ions are removed before the catalyst is used. This is achieved by washing the doped support, for example with water, after palladium, and, if present, gold have been converted into an insoluble form, for instance by reduction and/or precipitation with hydroxides.

Suitable solvents are all compounds in which the selected salts are soluble and which after impregnation can easily be removed again by drying. Suitable solvents for the acetates are, in particular unsubstituted carboxylic acids having from 2 to 10 carbon atoms, such as acetic acid, propionic acid, n- and iso-butyric acid and the various valeric acids. Owing to its physical properties and also for economic reasons, acetic acid is the preferred carboxylic acid. For the chlorides, water is particularly suitable. The additional use of a further solvent is advantageous if the salts are not sufficiently soluble in acetic acid or in water. Suitable additional solvents are those which are inert and miscible with acetic acid or water. Additives for acetic acid which may be mentioned are ketones such as acetone and acetylacetone, furthermore ethers such as tetrahydrofuran or dioxane, or else hydrocarbons such as benzene.

At least one salt of each of the three elements to be applied to the support particles (Pd/K/Cd, Pd/K/Ba, Pd/K/Au) has to be applied. A plurality of salts of one element can be applied, but in general exactly one salt of each of the three elements is applied.

The three elements to be applied in each case can be individually applied in the form of salt solutions, or otherwise in any combinations. Use is preferably made of a single solution which contains all three elements to be applied in the form of salts. Particular preference is given to the use of a single solution which contains exactly one salt of each of the three elements to be applied.

If general reference is made hereinafter to "the solution of the salts" the same applies analogously to the case in which use is made in order of a plurality of solutions which contain only part of the salts to be applied, with the individual parts adding up to the total amount of the salts which are to be applied to the support.

The solution of the salts is applied to the support particles by impregnating these once or a plurality of times with this solution, with the solution volume in each impregnation being more than 80% of the pore volume of the support particles. Subsequent to impregnation, the support particles are dried; in the case of a plurality of impregnations, drying is carried out after each impregnation.

The duration of each impregnation and also the time until commencement of the drying following this impregnation has to be selected so as to be sufficiently short for, after completion of the last drying, the specified metal salts to be present in an outer layer of from 5% to 80 % of the pore volume of the support particles.

The dynamic viscosity of the solution is at least 0.003 Pa.s, the upper limit is determined by the solubility of the salts used in the solvent selected. Preferably, the dynamic viscosity is from 0.005 to 0.009 Pa.s, in particular from 0.006 to 0.008 Pa.s.

If the solution volume selected is not sufficiently high for all support particles to be completely within the solution during impregnation, the support particles have to be intimately mixed during impregnation, for example in a rotating or agitated flask or a mixing drum, to ensure a uniform impregnated layer thickness in all support particles. The rotation rate or intensity of agitation has to, on the one hand, be high enough to ensure good mixing, but, on the other hand, must not be so high that the support material is significantly abraded.

A suitable method of determining the desired distribution of the impregnated layer thicknesses comprises cutting open a representative number of support particles and measuring impregnated layer thicknesses under a microscope. Here, preferably less than 5% of the particles should have an impregnated layer thickness which deviates by more than 15% from the average.

The solution of the salts should be at a temperature which is high enough to prevent precipitation of the salts during application to the support. However, the temperature should generally not be significantly above 70° C. to prevent excessive evaporation of the solvent.

During the drying of the support impregnated with the solution of the active catalyst components, it is advisable to match the temperature to the type of metal salts used. In the case of the acetates, which are frequently used for the production of Pd/K/Cd or Pd/K/Ba catalysts, drying is preferably carried out at reduced pressure. The temperature here should generally be from 50° to 80° C., preferably from 50° to 70° C. Furthermore, it is generally advisable to carry out the drying in an inert gas stream, for example in a nitrogen or carbon dioxide stream. In the case of the Pd/K/Au catalysts, which are generally impregnated with the corresponding chlorides, the drying can, in contrast, be carried out in a hot air stream at from 100° to 150° C. The residual solvent content after drying should preferably be less than 6% by weight for all three types of catalyst.

If a reduction of the palladium salt and, if applicable, of the gold salt is to be carried out, which is sometimes useful, this can be carried out using a gaseous reducing agent. The reduction temperature is generally between 40° and 260° C., preferably between 70° and 200° C. In general it is advantageous to carry out the reduction using a reducing agent diluted with inert gas, which contains from 0.01 to 50% by volume, preferably from 0.5 to 20% by volume, of reducing agent. The inert gas used can be, for example, nitrogen, carbon dioxide or a noble gas. Suitable reducing agents are, for example, hydrogen, methanol, formaldehyde, ethylene, propylene, isobutylene, butylene or other olefins. The amount of the reducing agent depends on the amount of palladium and, if applicable, on the amount of golds the reduction equivalent should be at least 1 to 1.5 times the oxidation equivalent, but larger amounts of reducing agent do no harm. Such a reduction is carried out subsequently to drying.

The preparation of vinyl acetate is generally carried out by passing acetic acid, ethylene and oxygen or oxygen-containing gases over the finished catalyst at temperatures of from 100° to 220° C., preferably from 120° to 200° C., and at pressures of from 1 to 25 bar, preferably from 1 to 20 bar, with unreacted components being able to be recirculated. The oxygen concentration is advantageously kept below 10% by volume (based on the gas mixture free of acetic acid). However, dilution with inert gases such as nitrogen or carbon dioxide is sometimes also advantageous. Carbon dioxide is particularly suitable for the dilution, since it is formed in small amounts during the reaction.

The catalysts of the invention make it possible for the process to be carried out more selectively than when using catalysts in which the support particles are impregnated right into the core ("impregnated through"), or make possible an expansion of capacity. To achieve expansion of capacity, it is possible to keep the reaction conditions (e.g. pressure, temperature, throughput, oxygen concentration) unchanged in comparison with the known catalysts, and to prepare more vinyl acetate per reactor volume and time. This makes the workup of the crude vinyl acetate obtained easier, since the vinyl acetate content in the exit gas from the reactor is higher, which leads further to a saving of energy in the workup section. A suitable workup is described, for example, in U.S. Pat. No. 5,066,365.

If, in contrast, the plant capacity is kept constant, the reaction temperature can be lowered and thereby the reaction can be carried out more selectively at the same total output, which saves starting material. Here the amount of carbon dioxide, which is formed as by-product and therefore has to be removed, and the loss of entrained ethylene associated with this removal are also smaller. In addition, this mode of operation prolongs the operating life of the catalyst.

The following examples illustrate the invention.

The catalyst support used was $SiO_2$ in the form of pellets having a diameter and a length of 6 mm in each case. The pellets were pressed from ®Aerosil powder with the aid of magnesium stearate as binder in accordance with DE-A 3 912 504. The surface area of the support was 120 $m^2/g$, its pore volume was 0.784 ml/g and its bulk density was 500 g/l. The pore volume of 1 l of support was 392 ml.

Comparative Example 1a 1 l of silica support was impregnated at 60° C. with a solution of 24.3 g of palladium acetate, 21.3 g of cadmium acetate and 23.8 g of potassium acetate in 392 ml of glacial acetic acid (solution volume=100% of the pore volume of the support). The material was subsequently dried in a drying cabinet at 200 mbar under nitrogen to a residual acetic acid content of 6% by weight; the drying temperature was 65° C. The finished catalyst contained 2.3% by weight of Pd, 1.8% by weight of Cd and 1.9% by weight of K.

A reaction tube having an internal diameter of 8 mm and a length of 1.5 m were charged with 50 ml of this catalyst. The gas to be reacted was then passed over the catalyst at a pressure of 8 bar (reactor inlet) and a catalyst temperature of 150° C. This gas comprised 27% by volume of ethylene, 55% by volume of nitrogen, 12% by volume of acetic acid and 6% by volume of oxygen. The results are shown in the table.

Comparative Example 1b 25.3 g of palladium acetate, 25 g of cadmium acetate and 25.3 g of potassium acetate were dissolved at 65° C. in 137.2 ml of acetic acid (solution volume=35% of the pore volume) and the highly viscous solution was placed in a reservoir preheated to 65° C. 1 l of catalyst support was likewise heated to 65° C. in a mixing drum able to be temperature controlled and was mixed at a rotation rate of 150 rpm. The impregnation solution was applied to the catalyst support by means of an ultrasound atomizer (100 kHz) over a period of 1 hour.

The material was subsequently dried as in Comparative Example 1a. The finished catalyst contained 2.3% by weight of Pd, 1.8% by weight of Cd and 1.9% by weight of K. The impregnated layer thickness was 0.8 mm.

The catalyst was tested as in Comparative Example 1a and the results are shown in the table.

Comparative Example 2a

The catalyst was produced as in Comparative Example 1a, except that now 4.0 g of barium acetate were applied in place of cadmium acetate. The finished catalyst contained 2.3% by weight of Pd, 0.4% by weight of Ba and 1.9% by weight of K.

The catalyst was tested as in Comparative Example 1a and the results are shown in the table.

Comparative Example 2b

The catalyst was produced as in Comparative Example 1b, except that now 4.3 g of barium acetate were used in place of cadmium acetate. The finished catalyst contained 2.3% by weight of Pd, 0.4% by weight of Ba and 1.9% by weight of K, the impregnated layer thickness was 0.8 mm.

The catalyst was tested as in Comparative Example 1a and the results are shown in the table.

Comparative Example 3a 1 l of silica support was, in accordance with EP-A-0 519 435, washed with 10% strength hydrochloric acid and then with water to remove the binder interfering with the formation of the impregnated layer and dried. The support was subsequently impregnated with a solution of 13.8 g of sodium chloropalladate and 4.0 g of tetrachloroauric acid in 392 ml of water. After drying with hot air at 150° C., 5.5 g of NaOH dissolved in 392 ml of water were added, to produce an impregnated layer by precipitation of palladium and gold. The material was subsequently stirred for 6 hours and allowed to stand for 16 hours at room temperature. After the support had been washed free of chloride with water and dried with hot air at 150° C., 35.1 g of potassium acetate in 392 ml of water were applied. After drying with hot air at 150° C. the catalyst contained 1.0% by weight of Pd, 0.4% by weight of Au and 2.8% by weight of K. The thickness of the impregnated layer produced by the treatment with sodium hydroxide solution was from 1.3 to 1.6 mm. The catalyst was tested in a Berty reactor at 152° C. using a gas mixture of 8% by volume of $O_2$, 37.5% by volume of $C_2H_4$, 15.7% by volume of HOAc and 38.8% by volume of $N_2$; the results are shown in the table.

Comparative Example 3b 13.8 g of sodium chloropalladate and 4.0 g of tetrachloroauric acid were dissolved in 78.4 ml of water (solution volume=20% of the pore volume). The solution was applied at room temperature to 1 l of catalyst support by means of an ultrasound atomizer (100 kHz) over a period of 1 hour; the material was subsequently dried in a hot air stream at 150° C. To precipitate palladium and gold, a solution of 5.5 g of NaOH in 78.4 ml of water was then applied to the impregnated support using the ultrasound atomizer. It was then, in the same way as in Comparative Example 3a, washed free of chloride and dried. It was subsequently reduced with $H_2$, impregnated with 35.1 g of potassium acetate in 392 ml of water and dried using hot air at 150° C.

The finished catalyst contained 1.0% by weight of Pd, 0.4% by weight of Au and 2.8% by weight of K; the impregnated layer thickness was 0.7 mm.

The catalyst was tested as in Comparative Example 3a and the results are shown in the table.

Example 1

759 g of palladium acetate, 750 g of cadmium acetate and 759 g of potassium acetate were dissolved at 65° C. in 3.9 l of acetic acid (solution volume about 10 times the pore volume) and the highly viscous solution (7 mPa.s) was placed in a reservoir preheated to 65° C. 1 l of the catalyst support was likewise heated to 65° C. and combined with the whole of the impregnation solution. After 3 minutes, the support particles were separated from the solution by means of a plastic screen.

Subsequently, drying was commenced within 3 minutes, which drying was otherwise carried out as in Comparative Example 1a. The finished catalyst contained 2.3% by weight of Pd, 1.8% by weight of Cd and 1.9% by weight of K. The impregnated layer thickness was 0.8 mm.

The catalyst was tested as in Comparative Example 1a and the results are shown in the table.

Example 2

The catalyst was produced as in Example 1, except that now 129 g of barium acetate were used in place of cadmium acetate. The finished catalyst contained 2.3% by weight of Pd, 0.4% by weight of Ba and 1.9% by weight of K, the impregnated layer thickness was 0.8 mm.

The catalyst was tested as in Comparative Example 1a and the results are shown in the table.

Example 3

690 g of sodium chloropalladate and 200 g of tetrachloroauric acid were dissolved in 3.92 l of water (solution volume about 10 times the pore volume). 1 l of catalyst support was impregnated, as described in Example 1, with this solution at room temperature for 3 minutes; subsequently drying in a hot air stream at 150° C. was commenced within 2 minutes. To precipitate palladium and gold, the impregnated support particles were then impregnated for 3 minutes with a solution of 275 g of NaOH in 3.92 l of water. They were then, in the same way as in Comparative Example 3a, washed free of chloride and dried. They were subsequently reduced with $H_2$, impregnated with 1755 g of potassium acetate in 3.92 l of water for 3 minutes, and drying in a hot air stream at 150° C. was commenced within 2 minutes.

The finished catalyst contained 1.0% by weight of Pd, 0.4% by weight of Au and 2.8% by weight of K; the impregnated layer thickness was 0.7 mm.

The catalyst was tested as in Comparative Example 3a and the results are shown in the table.

TABLE

| | Output [g/l h] | Spec. output (*) | Vinylacetate content % by weight in the condensed reactor exit gas | Selectivity [%] |
|---|---|---|---|---|
| Comp. Example 1a (Pd/K/Cd □) | 813 | 70.7 | 25.7 | 94.3 |
| Comp. Example 1b (Pd/K/Cd ○) | 915 | 79.6 | 33.0 | 96.3 |
| Comp. Example 2a (Pd/K/Ba □) | 827 | 71.9 | 25.9 | 92.8 |
| Comp. Example 2b (Pd/K/Ba ○) | 917 | 79.7 | 33.1 | 95.7 |
| Comp. Example 3a (Pd/K/Au #) | 710 | 142.0 | 22.6 | 89.3 |
| Comp. Example 3b (Pd/K/Au ○) | 740 | 148.0 | 24.2 | 90.0 |
| Example 1 (Pd/K/Cd) | 913 | 79.4 | 32.9 | 96.0 |
| Example 2 (Pd/K/Ba) | 912 | 79.3 | 32.9 | 95.9 |
| Example 3 (Pd/K/Au) | 743 | 148.6 | 24.3 | 90.8 |

*Gram of vinyl acetate per gram of palladium per hour
□ Catalyst impregnated right through to the core of the support particles
○ Surface impregnated catalyst produced by means of ultrasound spraying
Surface impregnated catalyst in accordance with EP-A-0 519 435 (precipitation with base)

Thus, essentially the same results are achieved in the Examples of the invention 1 to 3 as in the Comparative Examples 1b, 2b and 3b in which the catalysts were produced by ultrasound spraying. Surprisingly, it is therefore not at all necessary for the production of a very high performance surface impregnated catalyst to divide the impregnation solution into extremely fine droplets by means of the complicated use of ultrasound, but the impregnation of the invention is sufficient.

As the Comparative Examples 1a, 2a and 3a show, the performance data of impregnated-through catalysts or a surface impregnated catalyst in accordance with EP-A-0 519 435 are significantly worse.

What is claimed is:

1. A process for producing a surface impregnated catalyst comprising palladium, potassium and cadmium on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

2. The process as claimed in claim 1, wherein the dynamic viscosity of the solution is from 0.005 to 0.009 Pa.s.

3. A process for producing a surface impregnated catalyst comprising palladium, potassium and barium on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

4. The process as claimed in claim 3, wherein the dynamic viscosity of the solution is from 0.005 to 0.009 Pa.s.

5. A process for producing a surface impregnated catalyst comprising palladium, potassium and gold on porous support particles, which comprises impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

6. The process as claimed in claim 5, wherein the dynamic viscosity of the solution is from 0.005 to 0.009 Pa.s.

7. A surface impregnated catalyst comprising palladium, potassium and cadmium on porous support particles, obtainable by impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

8. A surface impregnated catalyst as claimed in claim 7, obtainable by the dynamic viscosity of the solution being from 0.005 to 0.009 Pa.s.

9. A surface impregnated catalyst comprising palladium, potassium and barium on porous support particles, obtainable by impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

10. A surface impregnated catalyst as claimed in claim 9, obtainable by the dynamic viscosity of the solution being from 0.005 to 0.009 Pa.s.

11. A surface impregnated catalyst comprising palladium, potassium and gold on porous support particles, obtainable by impregnating the support particles once or a plurality of times with at least one solution of at least one salt of each of the three elements and drying the support particles after each impregnation, with the dynamic viscosity of the solution being at least 0.003 Pa.s and the solution volume in each impregnation being more than 80% of the pore volume of the support particles, and with the duration of each impregnation and also the time until commencement of the drying following this impregnation being selected so as to be sufficiently short for, after completion of the last drying, the specified metal salts to be present in an outer layer of from 5% to 80% of the pore volume of the support particles.

12. A surface impregnated catalyst as claimed in claim 11, obtainable by the dynamic viscosity of the solution being from 0.005 to 0.009 Pa.s.

* * * * *